US005721359A

United States Patent [19]

Dunn et al.

[11] Patent Number: 5,721,359

[45] Date of Patent: Feb. 24, 1998

[54] CRYSTALLINE CEFTIOFUR FREE ACID

[75] Inventors: Michael J. Dunn, Paw Paw; Michael S. Bergren, Portage; Gregory E. Hardee; Kenneth Paul Shephard, both of Kalamazoo; Robert S. Chao, Portage; Jeffrey L. Havens, Mattawan, all of Mich.

[73] Assignee: Pharmacia & Upjohn Company, Kalamazoo, Mich.

[21] Appl. No.: 549,821

[22] PCT Filed: Mar. 7, 1994

[86] PCT No.: PCT/US94/01862

§ 371 Date: Sep. 11, 1995

§ 102(e) Date: Sep. 11, 1995

[87] PCT Pub. No.: WO94/20505

PCT Pub. Date: Sep. 15, 1994

Related U.S. Application Data

[63] Continuation-in-part of Ser. No. 33,291, Mar. 12, 1993, abandoned.

[51] Int. Cl.[6] .................... C07D 501/36

[52] U.S. Cl. .................... 540/227; 540/225

[58] Field of Search .................... 540/225, 227

[56] References Cited

U.S. PATENT DOCUMENTS

| | | | |
|---|---|---|---|
| 3,489,752 | 1/1970 | Crast, Jr. . | |
| 4,400,503 | 8/1983 | Yang . | |
| 4,464,367 | 8/1984 | Labeeuw et al. | 424/246 |
| 4,504,657 | 3/1985 | Bouzard et al. . | |
| 4,521,431 | 6/1985 | Crookes | 514/471 |
| 4,624,948 | 11/1986 | Dürckheimer | 514/206 |
| 4,877,782 | 10/1989 | Cazers et al. . | |
| 4,902,683 | 2/1990 | Amin et al. . | |
| 4,912,212 | 3/1990 | Ochiai et al. . | |
| 4,937,330 | 6/1990 | Sacks et al. . | |
| 4,973,684 | 11/1990 | Ochiai et al. . | |
| 5,013,713 | 5/1991 | Mitchell . | |
| 5,079,007 | 1/1992 | Putnam . | |
| 5,103,012 | 4/1992 | Heymes et al. . | |
| 5,134,137 | 7/1992 | Cazers et al. . | |

FOREIGN PATENT DOCUMENTS

| | | | |
|---|---|---|---|
| 0 278 656 | 8/1988 | European Pat. Off. | C07D 501/46 |

OTHER PUBLICATIONS

J. E. Hoover, Ed., *Dispensing of Medication,* 8th Ed., Mack Pub. Co., p. 72, 1976.

J. R. Robinson, Ed., *Sustained and Controlled Release Drug Delivery Systems,* Marcel Dekker, pp. 178–181, 1978.

V. H. Guerrini, et al., *Pharmacokinetic Evaluation of a Slow–Release Cefotaxime Suspension in the Dogand in Sheep,* Am. J. Vet. Res. 47(9):2057–2061, 1986.

*Primary Examiner*—Mukund J. Shah
*Assistant Examiner*—Pavanaram K. Sripada
*Attorney, Agent, or Firm*—Martha A. Gammill

[57] ABSTRACT

Anhydrous and crystalline free acid form of the cephalosporin antiobiotic ceftiofur, processes for its manufacture, and pharmaceutical composition containing it are provided.

24 Claims, 9 Drawing Sheets

C. CFA — Crystalline Ceftiofur Free Acid
A. CFA — Amorphous Ceftiofur Free Acid
C. HCl — Crystalline Ceftiofur Hydrochloride

CRYSTALLINE CEFTIOFUR FREE ACID

This application is a 371 of PCT/US/94/01862 filed on Mar. 7, 1994 and a C.I.P. of 08/033,291 filed on Mar. 12, 1993 now abandoned.

This invention relates to a novel crystalline form of ceftiofur free acid, a process for preparing this crystalline form, and a sustained-release pharmaceutical composition containing this crystalline form.

BACKGROUND OF THE INVENTION

Many cephalosporin compounds, derivatives thereof, and processes for their preparation, are known. For example, the following are known: amorphous cefuroxime axetil, its crystalline sodium salt, its naphthyridine derivative and its sesquihydrate (U.S. Pat. Nos. 4,820,833; 4,298,732; 4,442, 101); crystalline sodium cephemcarboxylate (U.S. Pat. No. 4,692,519); crystalline cephem heptahydrate (U.S. Pat. No. 4,555,404); crystalline cephalosporin di- or tri-hydrate (U.S. Pat. Nos. 4,812,561; 5,017,380; 4,933,443); cefadroxil monohydrate (U.S. Pat. No. 4,898,938); anhydrous crystalline ceftazidime and its pentahydrate (U.S. Pat. Nos. 4,624, 948; 4,616,080; EP 0 278 656); sodium amoxicillin pyrrolidone solvate (U.S. Pat. No. 4,318,852); cefazolin sodium monohydrate (U.S. Pat. No. 4,104,470); crystalline o-formylcefamandole (U.S. Pat. No. 4,006,138); salts of 3-acetoxymethyl-7-(iminoacetamido)-cephalosporanic acid derivatives, which may be either crystalline or amorphous (U.S. Pat. No. 5,103,012); crystalline monohydrate of 7-[D-α-amino-α-(p-hydroxyphenyl)acetamido]-3-methyl-3-cephem-4-carboxylic acid (U.S. Pat. No. 4,504,657); crystalline hydrochloride salt of syn-7-[[(2-amino-4-thiazolyl) (methoxyimino)acetyl]amino]-3-methyl-3-cephem-4-carboxylic acid (U.S. Pat. No. 4,400,503); crystalline cephem acid addition salts (Canadian Patent Application 2,018,794); crystalline (pivaloyloxy)methyl 7β-[2-(2-amino-4-thiazolyl)acetamido]-3-[[[1-[2-(dimethylamino) ethyl]-1H-tetrazol-5-yl]thio]methyl]-3-cephem-4-carboxylate (Chemical Abstracts 97:38761q (1982)); crystalline cephalexin (Chemical Abstracts 84:184895j (1976); crystalline cephalexin monohydrate (U.S. Pat. No. 3,531,481); crystalline 7-(D-2-naphthylglycylamido)-3-methyl-3-cephem-4-carboxylic acid tetrahydrate (U.S. Pat. No. 4,474,780); the preparation of a specific crystalline cephalosporin compound by stirring and the addition of methanol and butylacetate (Chemical Abstracts 110:212490z (1989)); a method for producing pure crystalline antibiotics products, such as penicillin and cephalosporin, by treating with ethanol in one or two steps (U.S. Pat. No. 4,912,211).

From the large number of patents and literature references that is available on cephalosporin compounds, it appears that the occurrence of an anhydrous or nonsolvated, non-salt, crystalline form of a cephalosporin compound is rare. Most such crystalline forms tend to be salts, hydrates, solvates or other derivatives thereof.

The cephalosporin antibiotic 7-[2-(2-amino-1,3-thiazol-4-yl)-2-methoxyimino)acetamido]-3-[(fur-2-ylcarbonyl) thiomethyl]-3-cephem-4-carboxylic acid (also named 7-[2-(2-amino-4-thiazolyl)-2-methoxyimino)-acetamido]-3-[2-(furanylcarbonylthiomethyl)-8-oxo-5-thia-1-azabicyclo [4.2.0]oct-2-ene-1-carboxylic acid) of the formula I in the Formula Chart below, its alkali metal, alkaline earth metal and amine salts of the carboxylic acid group, and easily hydrolyzable ester groups thereof are described and claimed in U.S. Pat. No. 4,464,367 (Labeeuw et al.). This cephalosporin free acid compound is now known by the generic name "ceftiofur." See also Merck Index, Eleventh Edition, 1948 (1989).

Ceftiofur Sodium is currently marketed by The Upjohn Company as NAXCEL® or EXCENEL® Sterile Solution to treat bovine respiratory disease (BRD). This product is administered intra-muscularly (IM) over a three to five day period using daily doses.

The free acid and cationic metal and amine salt and ester forms of this cephalosporin antibiotic are somewhat unstable chemically and are obtained as amorphous compounds which are difficult to purify, and are less desirable to work with in manufacturing pharmaceutical formulations containing them. This amorphous free acid and salts are difficult solids to isolate and handle in pharmaceutical manufacturing plants, which those in the pharmaceutical art would prefer to avoid.

However, it is not predictable how to make a specific crystalline form of a particular active drug compound. More specifically, it is not predictable how to make an anhydrous or nonsolvated, non-salt, crystalline form of a cephalosporin.

INFORMATION DISCLOSURE

U.S. Pat. No. 4,464,367 (Labeeuw et al.), as discussed above, discloses the preparation of the amorphous form of the ceftiofur free acid in Example 1(b).

U.S. Pat. No. 4,937,330 (Sacks et al.) discloses the preparation of the ceftiofur sodium salt by neutralizing the hydrochloride salt with a basic resin. The amorphous free acid is disclosed as an intermediate in this process.

U.S. Pat. No. 4,902,683 (Amin et al.) discloses and claims the hydrobromide and hydrochloride salts of ceftiofur, the crystalline form of the hydrochloride salt, processes for their preparation, and pharmaceutical compositions containing them for veterinary use. U.S. Pat. No. 5,079,007 (Putnam) discloses controlled-release antibiotic implants containing crystalline ceftiofur hydrochloride and amorphous ceftiofur sodium salt.

U.S. Pat. No. 4,877,782 (Cazers et al.) discloses zinc ceftiofur complexes which are useful as antibiotics especially in veterinary medicine. U.S. Pat. No. 5,143,137 (Cazers et al.) discloses disulfide derivatives of ceftiofur, which are useful as antibacterial agents especially in veterinary medicine.

U.S. Pat. Nos. 4,912,212 (Ochiai et al.) and 4,973,684 (Ochiai et al.) disclose cephem compounds having a residue of a nucleophilic compound at the 3-position.

U.S. Pat. No. 5,013,713 (Mitchell) discloses methods for the prolonged release of biologically active somatotropins.

U.S. Pat. No. 4,521,431 (Crookes) discloses a novel crystal form of ranitidine, designated Form 2, which has favorable filtration and drying characteristics over crystal Form 1.

Hoover, "Dispensing of Medication," 8th Ed., Mack Pub. Co. (1976); and J. R. Robinson Ed., "Sustained and Controlled Release Drug Delivery Systems," Marcel Dekker, (1978), disclose the technique for prolonging the release of a drug into the body by decreasing the solubility (by one or more techniques) of the drug, which decreases the dissolution rate if the drug is provided in a suspension.

V. H. Guerrini, et. al., "Pharmacokinetic evaluation of a slow-release cefotaxime suspension in the dog and sheep," Am. J. Vet. Res., vol. 47, no. 9, (1986) discuss the concept of sustained release formulations. Guerrini et al. discloses that the subcutaneous (sc) administration of cefotaxime in an oil suspension in dogs and sheep provides satisfactory and more prolonged plasma concentrations ($C_p$) than did aqueous preparation given intramuscular (im) (sheep only) or given sc (sheep and dogs).

None of these references disclose a crystalline form of ceftiofur which is anhydrous or non-solvated and which is a free acid or a non-salt.

SUMMARY OF THE INVENTION

The present invention particularly provides:

a crystalline compound of the formula I which is 7-[2-(2-amino-1,3-thiazol-4-yl)-2-methoxyimino)acetamido]-3-[(fur-2-ylcarbonyl)thiomethyl]-3-cephem-4-carboxylic acid;

in a composition comprising a compound of the formula I wherein the improvement is characterized by:

at least forty percent (40%) of the compound of formula I is crystalline;

a pharmaceutical composition which comprises a crystalline compound of the formula I; and a process for preparing a crystalline free acid of the formula I which comprises the steps of:

a) combining a solution of the compound of formula I in a water miscible solvent with water, which is at a temperature of between 20° C. and 60° C.

Throughout this document, the following terms have the indicated meanings:

By "sustained-release" is meant a formulation in which the drug becomes biologically available to the patient at a measured rate over a prolonged period.

By "pharmaceutically acceptable carrier or excipient" is meant any carrier or excipient that is commonly used in pharmaceutical compositions and are well known and readily prepared by one of ordinary skill in the art. Such carrier or excipient may be a solid or liquid and contain one or more suspending, dispersing, stabilizing, emulsifying, buffering, thickening, sweetening, flavoring, coloring or preservative agents.

"Solubility" is a direct consequence of a solid's structure and the intermolecular forces holding the solid together and is defined as the mount of drug which exists in solution when equilibrium is achieved between solution and solid state material.

"Dissolution rate" is the kinetic translation of solubility for a well stirred system under sink conditions.

"In-vivo release" is the biological consequence of the dissolution rate of a compound which is characterized by time to maximum concentration and the maximum concentration in the biological fluid of interest.

"Hygroscopity" is the ability of a compound to pick up moisture from or yield moisture to the atmosphere with changes in relative humidity.

This invention provides a crystalline form of 7-[2-(2-amino-1,3-thiazol-4-yl)-2-methoxyimino)acetamido]-3-[(fur-2-ylcarbonyl)thiomethyl]-3-cephem-4-carboxylic acid (also named 7-[2-(2-amino-4-thiazolyl)-2-methoxyimino)-acetamido]-3-[2-(furanylcarbonyl thiomethyl)-8-oxo-5-thia-1-azabicyclo[4.2.0]oct-2-ene-1-carboxylic acid), also known as ceftiofur, of formula I in the Formula Chart. The crystalline form of the present invention is more precisely described as a non-salt, crystalline form of ceftiofur that is anhydrous or nonsolvated.

As indicated above, the cephalosporin antibiotic can be named by either of two different nomenclature systems. Some prefer the more formal CHEMICAL ABSTRACTS system whereby the compound is named as a derivative of a "bicyclo" ring system. Some prefer the simpler "cephem" ring system nomenclature.

Crystalline organic compounds consist of a large number of atoms which are arranged in a periodic array in three-dimensional space. The structural periodicity normally manifests distinct physical properties, such as sharp, explicit spectral features by most spectroscopic probes (e.g., X-ray diffraction, infrared and solid state NMR). X-ray diffraction (XRD) is acknowledged to be one of the most sensitive methods to determine the crystallinity of solids. Crystals yield explicit diffraction maxima which arise at specific angles consistent with the lattice interplanar spacings, as predicted by Bragg's law.

On the contrary, amorphous materials do not possess long-range order. They often retain additional volume between molecules, as in the liquid state. Amorphous solids normally unveil a featureless XRD pattern with broad, diffuse halos because of the absence of the long range order of repeating crystal lattice.

Crystalline materials are preferred in most pharmaceutical applications. Crystalline forms are thermodynamically more stable than amorphous forms of the same substance. This thermodynamic stability is reflected in the lower solubility and improved physical stability of the crystalline form. The regular packing of the molecules in the crystalline solid denies the incorporation of chemical impurities. Hence crystalline materials generally possess higher chemical purity than their amorphous counterparts. The packing in the crystalline solid constrains the molecules to well defined lattice positions and reduces the molecular mobility that is the prerequisite for chemical reactions. Hence, crystalline solids, with very few notable exceptions, are chemically more stable than amorphous solids of the same molecular composition.

The crystalline ceftiofur free acid of the present invention has a distinct fourier transform infrared (FTIR) spectrum and a distinct powder X-ray diffraction (XRD) profile. By either means, the material is readily differentiated from other ceftiofur-containing solids, including crystalline ceftiofur hydrochloride salt, amorphous ceftiofur sodium salt, amorphous ceftiofur free acid, and amorphous ceftiofur zinc salt. The identity of the material as ceftiofur has been confirmed chromatographically and spectroscopically. The crystallinity of the material is confirmed by the presence of an XRD pattern. The XRD observations are corroborated by the observation of birefringence with polarized light microscopy. Birefringence is an accepted U.S. Pharmacopeia method of determining crystallinity. (U.S. Pharmacopeia and National Formulary, Vol. 22, page 1577, (1989)). The material exists as the unassociated free acid of ceftiofur, verified by the absence of chloride (present in the ceftiofur hydrochloride starting material).

Figure 1:
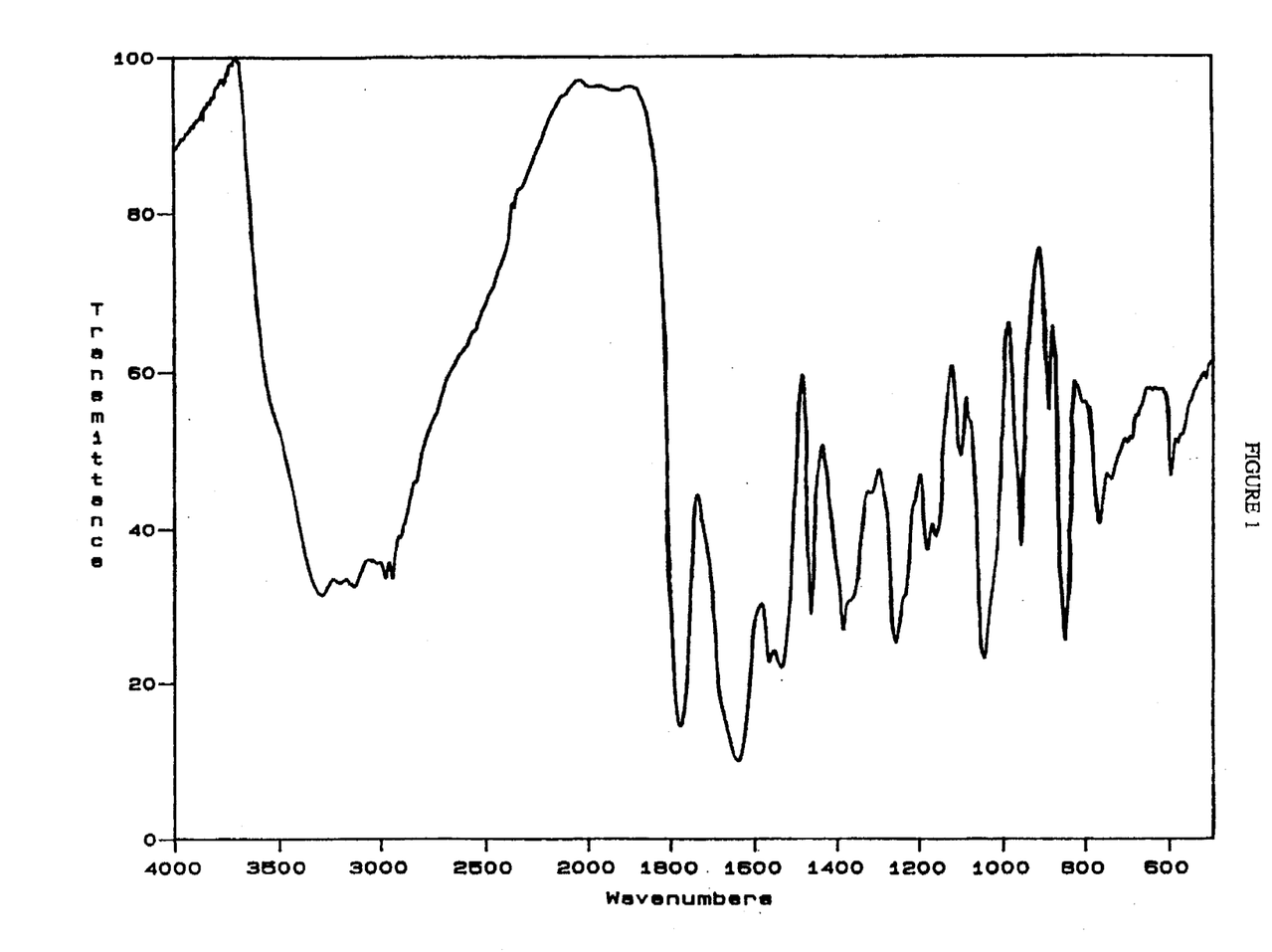
Figure 2:
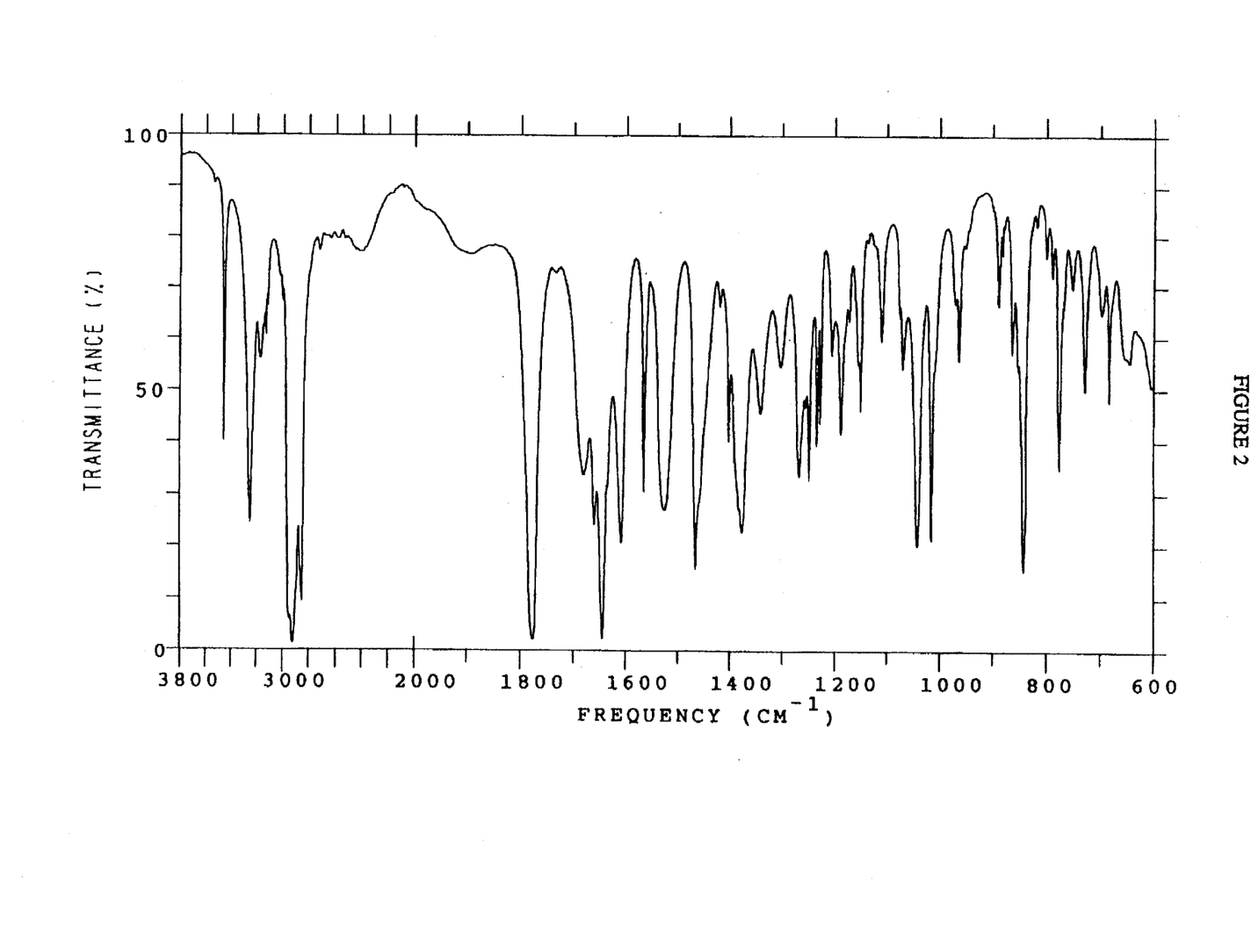
Figure 3:
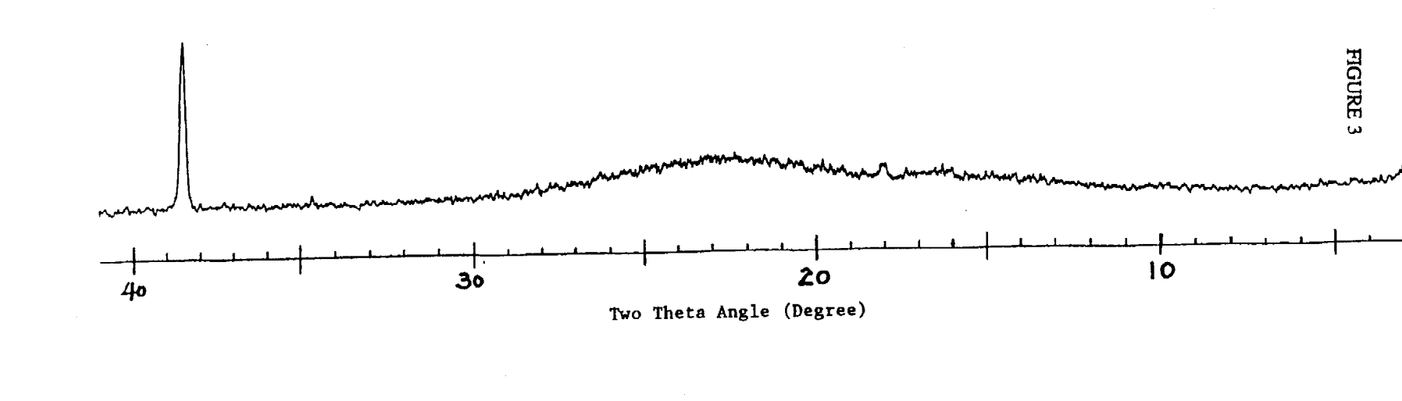
Figure 4:
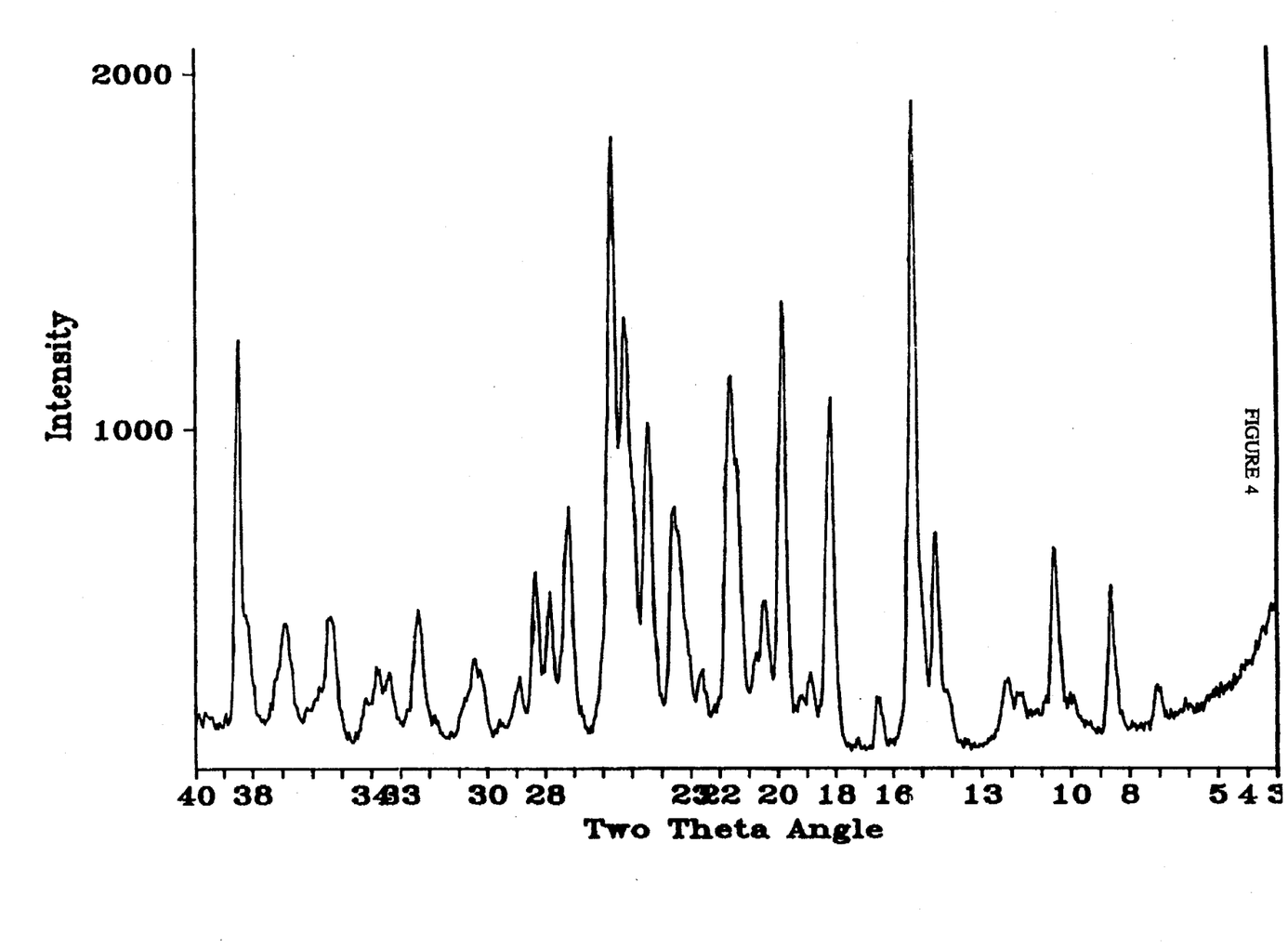
Figure 5:
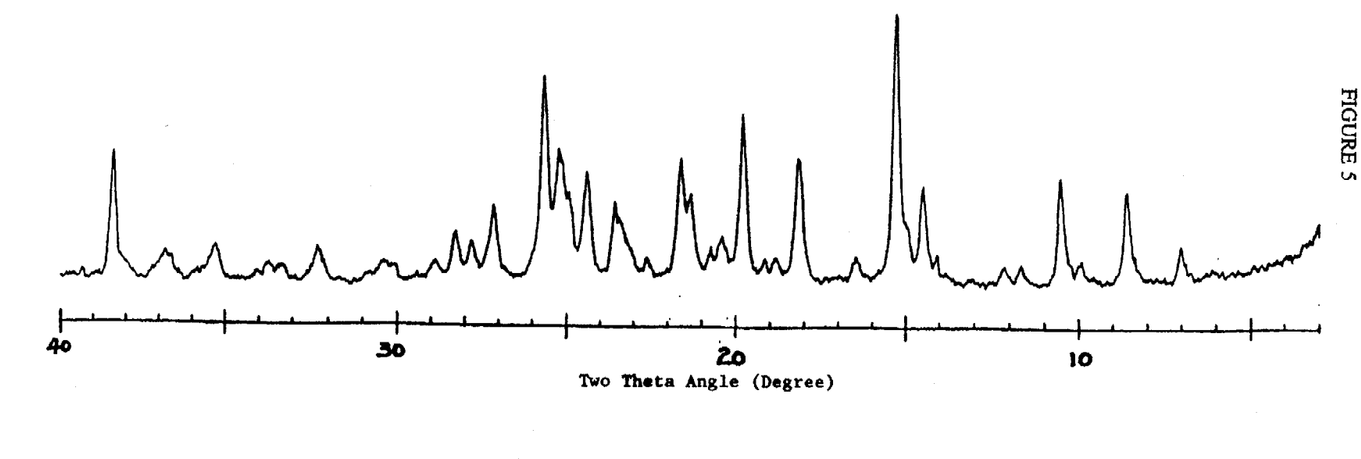

Representative FTIR and XRD patterns of the crystalline ceftiofur free acid of the present invention are shown in FIGS. 2, 4 and 5 below and of the amorphous ceftiofur free acid, prepared as described in Example 1(b) of U.S. Pat. No. 4,454,367, are shown in FIGS. 1 and 3 below. As would be apparent to one of ordinary skill in this art, the compound of FIG. 3 is in the amorphous form because of the broad, nondistinctive peaks in its XRD spectrum. FIG. 1, which is the FTIR spectrum for this compound, is consistent with this interpretation of FIG. 3. The compound of FIGS. 4 and 5 is in the crystalline form because of the sharp, distinctive peaks in its XRD spectra. FIG. 2, which is the FTIR spectrum for this compound, is consistent with this interpretation of FIGS. 4 and 5. Table I lists the characteristic diffraction peaks for the crystalline ceftiofur free acid of the present invention.

Furthermore, the crystalline ceftiofur free acid of the present invention, which contains an amino group and a carboxylic acid group, can also be written as a Zwitterion (or dipolar ion) as shown in formula IA of the Formula Chart below. Many of its physical and chemical properties, are consistent with the Zwitterion structure. It is a nonvolatile, crystalline solid which melts with decomposition at high temperatures; and it is insoluble in non-polar solvents, but is sparingly soluble in water. One of the most sensitive and convenient analytical methods used to identify the Zwitterion structure of a free amino acid is the infrared spectroscopy (IR). For example, asymmetric and symmetric stretching modes of the $NH_3^+$ ion are assigned at about 3250 and 2600–2400 $cm^{-1}$, respectively, while the carboxylate $COO^-$ ion stretching vibration locates at about 1565 $cm^{-1}$. It is noteworthy that the C=O stretching mode of a normal carboxylic acid (not an amino acid) appears at about the 1750–1700 $cm^{-1}$ spectral range. The IR of crystalline ceftiofur free acid of the present invention at solid phase (see FIG. 2 below) is totally consistent with the Zwitterion structure of formula IA.

The crystalline ceftiofur free acid of the present invention has advantageous physical-chemical properties. It has lower solubility in aqueous solvents than its crystalline hydrochloride salt staffing material. The lower solubility is believed to contribute to its slow dissolution rate and its sustained release properties in-vivo, as discussed further in the Examples below. Also, both its hygroscopicity and stability (in bulk and formulations) are superior to other ceftiofur salts, such as the crystalline hydrochloride salt and the amorphous free acid. Additionally, the crystalline free acid is considerably more stable, has improved processing characteristics, and can be dried more easily due to its increased stability at elevated temperatures. All of these properties are very useful when formulating a pharmaceutical product from the crystalline free acid.

A comparison of these physical-chemical properties of the crystalline ceftiofur free acid of the present invention, of the amorphous ceftiofur free acid, prepared as described in Example 1(b) of U.S. Pat. No. 4,464,367, and of the crystalline ceftiofur hydrochloride salt is summarized in Table II below. From this table, it is apparent that the measurable properties of the crystalline free acid of the present invention are distinctly different from and superior to those of the amorphous free acid and the crystalline hydrochloride salt. Also, from this table, it is apparent that while the physical-chemical properties of a compound may be expected to improve as a consequence of going from an amorphous form to a crystalline form, the favorable characteristics of crystalline ceftiofur free acid relative to crystalline ceftiofur hydrochloride salt were unpredictable and unanticipated. Surprisingly and unexpectedly, the crystalline free acid of the present invention is anhydrous, whereas the crystalline hydrochloride salt exists as either the hemihydrate or the monohydrate, or as a mixture of the two, at normal ambient relative humidity. The anhydrous nature of the free acid lends itself to improved formulation characteristics. Also, as further demonstrated in the Examples below, crystalline free acid has sustained release properties in vivo while the crystalline hydrochloride does not have useful sustained release properties.

Another property of these ceftiofur compounds, which is compared in Table II, is their thermal stability (differential scanning calorimetry (DSC) decomposition temperature). (The decomposition temperatures given below and in Table II are approximate and are the result of a single reading from typical lots of these compounds.) Ceftiofur is thermally unstable in the solid-state at high temperatures. Liquefaction is accompanied by decomposition. Under these circumstances, it is more useful to compare decomposition temperatures than melting temperatures, because the sample decomposes before the melting process is complete. DSC is a convenient technique for monitoring the heat evolved during sample decomposition. The peak decomposition temperatures and the onset of decomposition can be extracted from the profile of heat flow as a function of temperature.

Decomposition of ceftiofur free acid and ceftiofur hydrochloride salt is exothermic and occurs in two stages. The first stage of decomposition occurs at lower temperatures and is largely complete before the second stage begins. The first stage of decomposition produces an exothermic peak in the DSC at a temperature that depends on the solid phase. The onset for this peak is typically measured as an intersection of the baseline and the peak upslope. Since the onset provides a good estimate of the temperature where decomposition begins, it reflects the thermal stability of the solid phase.

Under the typical DSC scan conditions of 5° C./minute, the onset temperature for a typical sample of amorphous ceftiofur free acid was about 144° C. The broad decomposition exotherm had a peak temperature of about 177° C. Under the same conditions, the onset temperature for a typical sample of crystalline ceftiofur free acid was about 212° C., and the peak temperature was about 222° C. The increased onset temperature for the crystalline ceftiofur free acid reflects a large enhancement in the thermal stability of the crystalline phase as a consequence of the regular packing of molecules in the crystalline lattice.

As noted above, ceftiofur hydrochloride salt is another crystalline solid containing the ceftiofur molecule. At the DSC scan rate of 5° C./minute, the onset temperature for thermal decomposition in a typical sample of ceftiofur hydrochloride salt was 187° C., and the peak temperature was 192° C. Surprisingly and unexpectedly, the crystalline ceftiofur free acid has better thermal stability, as measured by DSC, than the crystalline hydrochloride salt.

Thus, as discussed above, it is not predictable what properties a crystalline compound will have. Furthermore, and as exemplified below, it is not predictable how to prepare the crystalline form of any given compound.

Typically to achieve the crystalline form of an organic compound, the compound is placed in an organic solvent in which it is minimally soluble at room temperature, and then heated to obtain a solution of the compound. The solution is cooled down and during this cooling period, the compound will crystallize out.

The preparation of crystalline ceftiofur hydrochloride is considered to involve a typical crystallization. Several methods for the preparation of ceftiofur hydrochloride are described in U.S. Pat. No. 4,902,683. In one readily used method, once the hydrochloride salt is obtained by adding hydrochloric acid to a water/acetone solution of ceftiofur, the resulting solution is cooled slowly to obtain crystalline ceftiofur hydrochloride.

However, the preparation of crystalline ceftiofur free acid of the present invention provides a surprising and unique approach to the preparation of a crystalline compound. In the process of the present invention, heat is necessary to induce crystallization of ceftiofur free acid. For example, in one readily used method of the present invention, a tetrahydrofuran solution of ceftiofur free acid is added to hot water with stirring. Initially, the ceftiofur free acid precipitates out as an amorphous solid; however, continued stirring and heating of the solution results in the formation of crystalline ceftiofur free acid, which is a single polymorph.

Such a method for inducing the crystallization of a compound is not typical. In fact, when a chemist places an organic compound in an organic, water-miscible solvent, and dilutes this solution with water to cause precipitation (commonly termed "water knockout"), one would most commonly expect to obtain an amorphous, not a crystalline, compound.

More specifically, the crystalline form of ceftiofur free acid of the present invention is prepared by combining the crystalline ceftiofur hydrochloride of formula II, prepared as described in U.S. Pat. No. 4,902,683, which is hereby incorporated by reference herein, with any of several different organic/aqueous solutions, including 1:1 solutions of water with a water miscible solvent, such as acetone, acetonitrile, methanol, tetrahydrofuran (THF) or isopropanol, or a 3:7 solution of water with a water miscible solvent, such as ethanol. The use of the polyvinylpyridine resin to neutralize the hydrochloride salt of ceftiofur is further described in U.S. Pat. No. 4,937,330 (Sacks et al.), which is hereby incorporated by reference herein.

The preferred procedure for the preparation of crystalline ceftiofur free acid begins with crystalline ceftiofur hydrochloride, which is treated with polyvinylpyridine resin in a tetrahydrofuran-water mixture to remove the hydrochloride from ceftiofur. After filtration of this mixture to remove the polyvinylpyridine resin, the filtrate is added slowly to water, which is preferred, or the water is added to the filtrate. The water must be at a temperature of between 20° C. and 60° C. Preferably, the water is at a temperature of between 40° C. and 60° C. Most preferably, the water is at approximately 50° C. The ratio of water to filtrate is in the range of 10:1 to 2:1. Preferably, the ratio of water to filtrate is approximately 3:1. This mixture is then stirred for a time period of between thirty (30) minutes and twenty-four (24) hours. Preferably, it is stirred for a time period of between thirty (30) minutes and four (4) hours. More preferably, it is stirred for approximately two (2) hours. Most preferably, it is stirred for between thirty (30) minutes and one (1) hour. Finally, the mixture is filtered, preferably immediately, and dried by procedures well known to one of ordinary skill in the art to obtain the crystalline free acid of the present invention. Example 3 below is the most preferred process for the preparation of the crystalline free acid of the present invention.

By modifying the above described procedure, (e.g., length of heating and stirring) compositions of ceftiofur free acid, containing varying percentages of crystalline free acid, may be obtained. For example, longer periods of heating and stirring typically result in compositions containing more crystalline free acid. Compositions containing at least forty percent (40%) or fifty percent (50%) of the crystalline free acid are preferred, with compositions containing at least seventy percent (70%) being most preferred.

The crystalline ceftiofur free acid of the present invention is useful as the active antibiotic drug compound in pharmaceutical dosage forms for treating valuable mammalian animals and humans to treat bacterial infections in that valuable animal or human. Presently it is contemplated that this compound will be especially useful as a veterinary antibiotic drug to treat valuable animals such as cattle, swine, horses, sheep, goats, dogs and cats to fight the effects of bacterial infections caused by susceptible organisms, such as *Pasturella hemolitica*, *Pasturella multiocida*, *Salmonella typhimurium*, *Salmonella choleraeasuis*, *Actinbacillus plearopneumoniae*, *Streptococcus suis*, *Haemophilus somnus*, *E. coli*, *Staphylococcus aureus* and the like, some of which are commonly associated with diseases in animals, such as bovine respiratory disease and swine respiratory disease.

The term "dosage unit form" as used in this specification refers to physically discrete units suitable as unitary dosages for mammalian subjects, each unit containing as the essential active ingredient a predetermined quantity of the crystalline ceftiofur free acid of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification. Examples of suitable dosage unit forms in accordance with this invention are liquid preparations in suitable liquid vehicles for intramuscular, intramammary and intravenous administration, suppositories and sterile dry preparations for the extemporaneous preparation (mixing just prior to administration) of sterile injectable preparations in a suitable liquid vehicle or for administration as a solid implant. Suitable solid diluents or carriers for the solid pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Liquid preparations are prepared in water or aqueous vehicles which advantageously contain suspending agents, for example, methylcellulose, alginates, tragacanth, pectin, kelgin, cartagenan, acacia, polyvinylpyrrolidone, polyvinyl alcohol, and the like, to increase the viscosity of the composition. Additionally for injectable forms, the formulation must be sterile and may be fluid to the extent that easy syringeability exists or may be solid for implants. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, benzoic acid, phenol, thimerosal, and the like to preserve the composition against microorganisms. In many cases, it is preferable to include osmotically active agents, for example, sugars or sodium chloride in isotonic concentrations. Carriers and vehicles include vegetable oils, dimethylacetamide, dimethylformamaide, ethyl lactate, ethyl carbonate, isopropyl myristate, ethanol, polyols, for example, glycerol, propylene glycol, liquid polyethylene glycol, and the like. Any solid preparations for subsequent extemporaneous preparation of sterile injectable preparations are sterilized, by exposure to heat, cobalt 60 irradiation, or by exposure to a sterilizing gas, for example, ethylene oxide. The aforesaid carriers, vehicles, diluents, surfactants, excipients, preservatives, isotonic agents and the like constitute the pharmaceutical means which adapt the preparations for systemic administration.

The various pharmaceutical dosage forms exemplified in U.S. Pat. No. 4,902,683 (Amin et al.), especially columns 9–16, and the antibiotic implants disclosed in U.S. Pat. No. 5,079,007 (Putnam), are also hereby incorporated by reference herein.

Due to the lower solubility of the crystalline ceftiofur free acid, its rate of dissolution is slower. As a result the absorption rate is less, and thus various controlled release or sustained-release formulation(s) can also be prepared using it. A controlled release or sustained-release formulation can be more conveniently given once per treatment as opposed to being given daily with other formulations. For example, Ceftiofur Sodium, which is currently marketed as NAX- CEL® or EXCENEL® Sterile Solution, is administered IM in daily doses over a three to five day period.

Using the criteria for sustained release as the time which plasma concentrations remain above some minimum concentration ($t_{>0.2}$), a comparison of various derivatives of ceftiofur can be made. In aqueous formulations, an inverse rank order correlation is seen (as expected from solubility data) between the aqueous solubility at neutral pH and the time above the selected minimum concentration for the ceftiofur salts (sodium<crystalline hydrochloride<crystalline free acid<zinc). In oil formulations, an unexpected order of duration is seen (sodium<crystalline hydrochloride<zinc<crystalline free acid), with the crystalline free acid being the longest. This difference is of practical and statistical significance. Since the crystalline hydrochloride had much greater solubility than the crystalline free acid, this data shows the sustained-release property of the crystalline free acid, especially in oil formulations, which is further exemplified in Examples 5 and 6 below.

The preparation of such oil formulations is well known to one of ordinary skill in the formulation art. Conventional oil formulations and methods for their preparation are set forth in U.S. Pat. No. 5,013,713 (Mitchell), which is hereby incorporated by reference herein, specifically, column 6, lines 17–59; column 7, lines 22–37; column 7, line 48, through column 8, line 4; and column 9, line 59, through column 10, line 23. Preferred oils include corn oil, peanut oil, sesame oil, olive oil, palm oil, safflower oil, soybean oil, cottonseed oil, rapeseed oil, sunflower oil and mixtures thereof. Most preferred is cottonseed oil.

As mentioned above, the compositions of the present invention are useful for parenteral administration, e.g., by injection intraperitoneally or, more preferably, subcutaneously or intramuscularly. Also as mentioned above, the duration of sustained-release is that period of time during which the active drug is delivered at the rate required for the desired biological effect, typically indicated by the concentration of the drug in the mammal's circulating blood stream.

The pharmaceutical dosage unit forms of the crystalline ceftiofur free acid (active ingredient) of the present invention are prepared in accordance with the preceding general description to provide to the mammal undergoing treatment from about 1.1 to 6 mg/kg of the active ingredient per dosage unit form. The preferred dosage is about 2 to 6 mg/kg of the active ingredient, with about 4.4 mg/kg being the most preferred dosage, especially for bovine or swine respiratory disease. Variations in the above dosages of crystalline ceftiofur free acid for the specific mammal and/or disease being treated would be readily known and apparent to one of ordinary skill in the art of veterinary medicine.

Furthermore, the mount of the active ingredient provided in the pharmaceutical dosage unit forms is that amount sufficient to obtain the antibiotic effects within the aforesaid effective non-toxic dosage ranges. For example, the injectable formulations of the crystalline ceftiofur free acid of the present invention, as described above, preferably have a concentration of active ingredient of from about twenty (20) to two hundred (200) mg/ml in order to provide to the mammal being treated the appropriate dosage of the active ingredient, as described above.

DETAILED DESCRIPTION OF THE INVENTION

The invention is further illustrated by the following detailed examples.

FTIR Experimental Conditions:

A. The infrared spectrum of the sample of Example 1 was collected using a Matsan Galaxy 5020 FTIR spectrometer. The sample was prepared as a 1% potassium bromide (KBr) pellet for data acquisition. Important instrumental parameters are listed below:

Resolution: 2 $cm^{-1}$
Sensitivity: 1
Infrared Range: 4000–600 $cm^{-1}$

The infrared spectrum of FIG. 1 below was collected using this procedure. The resulting FTIR spectrum of this sample is consistent with the determination that it was amorphous.

B. The infrared spectrum of the sample of Example 2 was collected using a Digilab FTS-40 FTIR spectrometer. The sample was prepared as mineral oil dispersion for data acquisition. Important instrumental parameters are listed below:

Resolution: 2 $cm^{-1}$
Coadded Scan: 16
Apodization: Boxcar Function
Detector: MCT-B
Sensitivity: 1
Infrared Range: 4000–600 $cm^{-1}$ The infrared spectrum of FIG. 2 below was collected using this procedure. The resulting FTIR spectrum of this sample is consistent with the determination that it was crystalline.

XRD Experimental Conditions:

A. A Rigaku DMAX-A X-ray diffractometer was used for the acquisition of powder XRD pattern for the sample of Example 2. The instrument uses the copper radiation with a nickel filter (CuKα, 1.5406 A). Major instrumental parameters are set as follows: 40 KV voltage, 30 mA power, beam aperture of 1° and detector aperture (receiving slit) of 0.30 mm. All patterns were scanned over the spectral range of 3°–40° two-theta angles with a scan rate of 1.5° two-theta/min (step size of 0.05° and counting time at 2 second/step). Each XRD scan produced an ASCII file which was then converted (with a Galactic's SpectraCalc software) to a binary format for data analysis and output. The sample was ground to fine powders and packed into an aluminum tray.

The XRD pattern of FIG. 4 and Table 1 below were collected using this procedure. The resulting XRD pattern of this sample indicated that it was crystalline.

B. A Siemens D-500 diffractometer was used for acquisition of the powder XRD patterns for samples of Examples 1 and 2. The instrument uses the copper radiation with a nickel filter (CuKα). Other parameters were set as follows: 40 KV voltage, 30 mA power, beam aperture of 0.3°, detector aperture of 0.05°, and a continuous scan rate of 2° two-theta/min. The chart rate of strip char recorder was set at 1.0° two-theta/cm. The spectral range is 3°–40° two-theta. The sample was ground to fine powders, if necessary, and then packed into sample tray.

The XRD patterns of FIGS. 3 and 5 below were collected using this procedure. The sample for FIG. 3 was a hand-ground, tan powder. Its resulting XRD pattern indicated that it was amorphous. The sample for FIG. 5 was a tan powder. Its resulting XRD pattern indicated that it was crystalline.

EXAMPLE 1

Preparation of Amorphous Ceftiofur Free Acid

Using the procedure described in Example 1(b) of U.S. Pat. No. 4,464,367 (Labeeuw et al.) (assigned to Sanofi, Paris, France), the ceftiofur free acid was obtained as follows:

A mixture of 50 g of tritylated ceftiofur, 83 ml of formic acid, and 83 ml of water is heated to 53° C. to 58° C. and stirred at this temperature for 30 minutes. This slurry is filtered and the solids washed with 83 ml of 70/30 formic acid/water. The filtrate is diluted with 334 ml of ethanol and concentrated down to an oil under vacuum. This material is dried under vacuum for 60 hours. The resulting foam is slurried with 167 ml of ethanol. This slurry is filtered and washed with diethyl ether. The solids are dissolved in 835 ml of acetone and 1567 ml of ethanol. This solution is concentrated under vacuum to a volume of 167 ml. This slurry is cooled to 25° C. and filtered. The solids are washed twice with ethanol and twice with ether. These solids are dried at more temperature to give about 15.1 g of amorphous ceftiofur free acid.

Physical characteristics are as follows:
FTIR spectrum: FIG. 1 below.
XRD: FIG. 3 below.

The FTIR and XRD spectra indicate that the title product is amorphous (noncrystalline).

EXAMPLE 2

Preparation of Crystalline Ceftiofur Free Acid

A slurry of 75.12 g of ceftiofur hydrochloride in 375 ml of tetrahydrofuran and 37.5 ml of water is stirred at room temperature for 1 hour. To this slurry is added 37.5 g of polyvinylpyridine resin and 225 ml of tetrahydrofuran. The resulting mixture is stirred at room temperature for 30 minutes and then filtered. The resin is washed with 150 ml of tetrahydrofuran. The filtrate is heated to >45° C. and diluted with 1075 ml of 50° C. water. To this cloudy solution is added 2.25 g of crystalline ceftiofur free acid and the resulting mixture is stirred for about 10 minutes. This slurry is then diluted further by the slow addition of 905 ml of water while maintaining the temperature at >45° C. The resulting slurry is stirred at 50°–55° C. for thirty (30) minutes to one (1) hour and is gradually cooled to 19° C. and filtered. The solids are washed with water and dried with nitrogen to give about 65 g of crystalline ceftiofur free acid (which is approximately 94.5% crystalline).

Physical characteristics are as follows:
FTIR spectrum: FIG. 2 below.
XRD: FIGS. 4 and 5 below.

The FTIR and XRD spectra indicate the title product is crystalline. Table I below lists the characteristics diffraction peaks for the crystalline ceftiofur free acid of the present invention.

EXAMPLE 3

Preparation of Crystalline Ceftiofur Free Acid

Ceftiofur hydrochloride (17.1 g) is slurried for at least one hour at room temperature with 70 ml of tetrahydrofuran and 5.1 ml of water. To this slurry are added 8.6 g of PVP resin followed by 60 ml of tetrahydrofuran. After stirring for 45 minutes this slurry is filtered. The PVP resin is washed with two 31 ml portions of tetrahydrofuran. The filtrate is then added slowly over a period of about one hour to 515 ml of water at 45°–55° C. This slurry is stirred at 45°–55° C. for 30 minutes and filtered immediately at the end of the addition. The solids are washed with 70 ml of water and dried at 50° C. to give 13.5 g of crystalline ceftiofur free acid.

EXAMPLE 4

Sustained-Release Oil Formulation

An example of a sustained-release formulation, containing the crystalline ceftiofur free acid of the present invention, which is prepared by procedures readily known to one of ordinary skill in the formulation art, has the following ingredients:

Ceftiofur Free Acid (Crystalline) 100 mg activity per milliliter
Lecithin (Phospholipon 90-H) 0.5 mg per milliliter
Sorbitan Mono-oleate (Span 80) 1.5 mg per milliliter
Cottonseed Oil q.s.

EXAMPLE 5

Plasma Disposition of Sustained-Release Aqueous Suspensions of Ceftiofur Crystalline Free Acid in Cattle Sixteen Holstein calves were administered ceftiofur crystalline free acid in an aqueous suspension (100 mg/mL) by the intramuscular (IM) or subcutaneous (SC) route of administration as a single dose of 1.1 mg ceftiofur activity/ kg in a crossover study (each calf got each treatment), with a two-week washout between doses. Blood samples were obtained serially for 120 hours for analysis of ceftiofur and metabolites (measured as desfuroylceftiofur acetamide by HPLC). The primary decision variable was the time ceftiofur metabolite concentrations remained above 0.2 µg/mL ($t_{>0.2}$), with secondary decision variables being "relative area under the concentration-time curve" (AUC) of the treatments and injection site irritancy assessed antemortem by visual and manual inspection of the injection sites over time. Both $t_{>0.2}$ and AUC were calculated using both the predictive pharmacokinetic equation method and the direct graphical method of trapezoids (AUC) and log linear interpolation ($t_{>0.2}$).

The $t_{>0.2}$ for ceftiofur crystalline free acid aqueous suspension was 26.98 h after IM and 30.43 h after SC administration (P=0.257).

EXAMPLE 6

Plasma Disposition of Sustained-Release Oil Suspensions of Ceftiofur Crystalline Free Acid in Cattle: Comparison to Aqueous Solution of Ceftiofur Sodium Sixteen Holstein calves were administered ceftiofur crystalline free acid in an oil suspension (100 mg/mL) or ceftiofur sodium (NAXCEL® Sterile Powder) as an aqueous solution (50 mg/mL) subcutaneously (SC) in a crossover study (each calf received each treatment), with a two-week washout period between doses (2.2 mg ceftiofur activity/kg body weight). Blood samples were obtained serially for 120 hours after drug administration for analysis of ceftiofur and metabolites (measured as desfuroylceftiofur acetamide by HPLC). The primary decision variable was the time ceftiofur metabolite concentrations remained above 0.2 µg/mL ($t_{>0.2}$), with secondary decision variables being "relative area under the concentration-time curve" (AUC) of the treatments and injection site irritancy assessed antemortem by visual and manual inspection of the injection site over time. Both $t_{>0.2}$ and AUC were calculated using both the predictive pharmacokinetic equation method and the direct graphical method of trapezoids (AUC) and log-linear interpolation ($t_{>0.2}$).

The oil suspension of ceftiofur crystalline free acid was equally bioavailable with the aqueous solution of ceftiofur sodium when both were administered subcutaneously (P>0.05). When compared to the $t_{>0.2}$ for ceftiofur sodium (45.50 h), the $t_{>0.2}$ for ceftiofur crystalline free acid (121.58 h) was significantly longer (P<0.0001). The terminal phase half-life (corresponding to the absorption phase in this flip-flop pharmacokinetic model) of the crystalline free acid in oil was also longer.

EXAMPLE 7

In Vitro Dissolution of Ceftiofur Oil Suspension Formulations 100 mg samples of crystalline ceftiofur free acid, amorphous ceftiofur free acid (prepared as described in Example 1) and crystalline ceftiofur hydrochloride, which were all prepared as oil formulations as described in Example 4 above, were loaded into teflon dissolution cells and sealed with a constant surface area dialysis membrane. The loaded cells were placed in a standard dissolution apparatus containing 500 ml of pH 7 aqueous dissolution media which was stirred by a 50 RPM rotating paddle.

Figure 6:
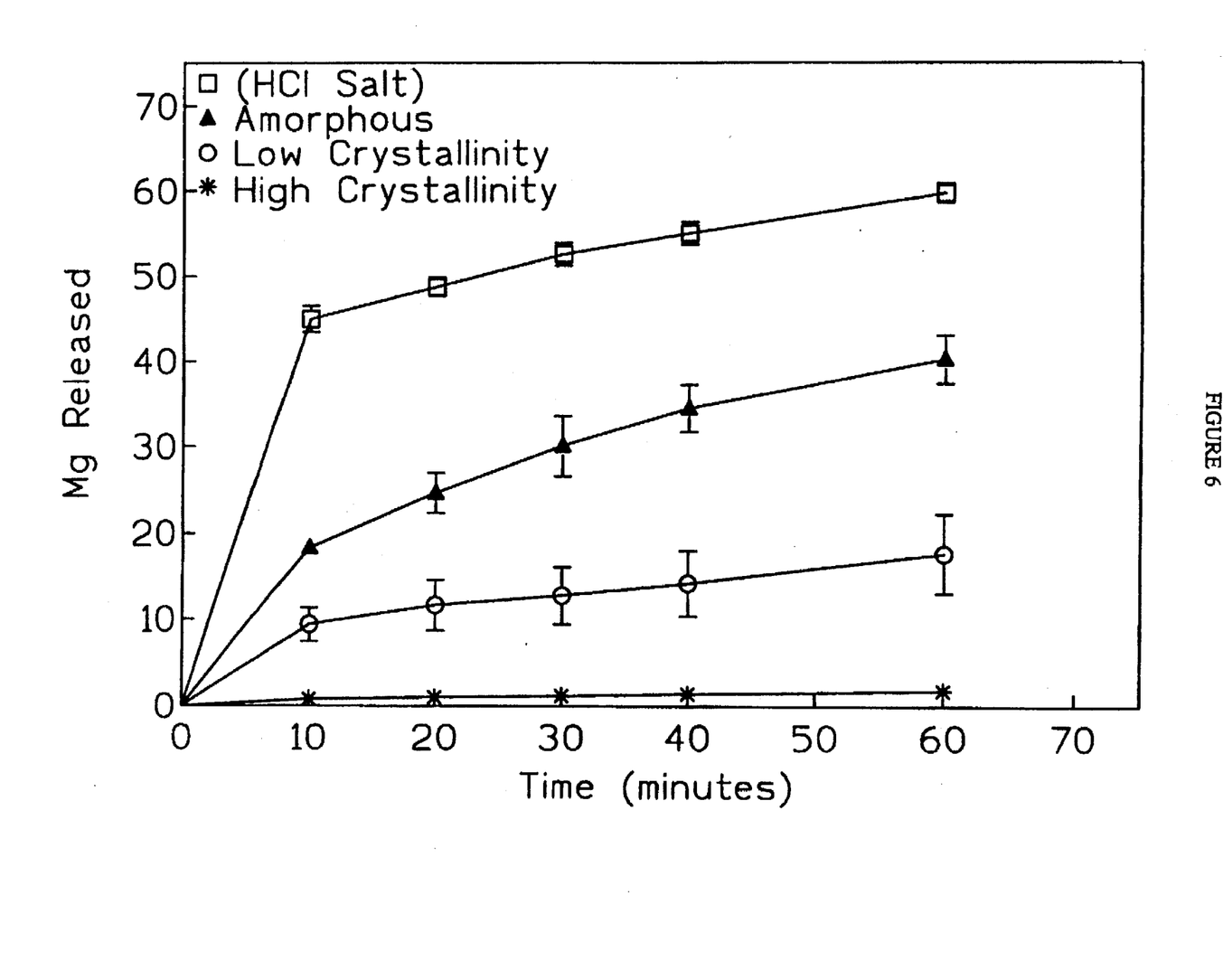

The results obtained are shown below in FIG. 6 below. (In FIG. 6 all formulations are 100 mg/ml. One standard deviation is shown. The sample designated low crystallinity was approximately 32.7% crystalline by XRD; the sample designated high crystallinity was approximately 74.7% crystalline by XRD.) The formulations containing the crystalline ceftiofur hydrochloride and the amorphous ceftiofur free acid show very fast release from the formulation into the dissolution media. The formulations of crystalline ceftiofur free acid, especially the highly crystalline sample, shows a significantly reduced release of drug into the aqueous dissolution compartment.

EXAMPLE 8

Plasma Disposition of Ceftiofur Free Acid Oil Suspensions Administered Subcutaneously in Cattle Cattle were administered a single subcutaneous dose (4.4 mg/kg body weight) of crystalline ceftiofur free acid and amorphous ceftiofur free acid (both prepared and then formulated as described above in Examples 1, 3 and 4). The concentration of plasma ceftiofur and desfuroylceftiofur related metabolites were determined over time for 120 hours. The primary decision criteria (that most related to efficacy) was considered to be the time that the ceftiofur metabolite concentrations remained above 0.2 mcg/ml ($t_{>0.2}$). Less important parameters calculated included "area under the concentration-time curve" (AUC) for each treatment and time to maximum concentrations ($t_{max}$).

Figure 7:
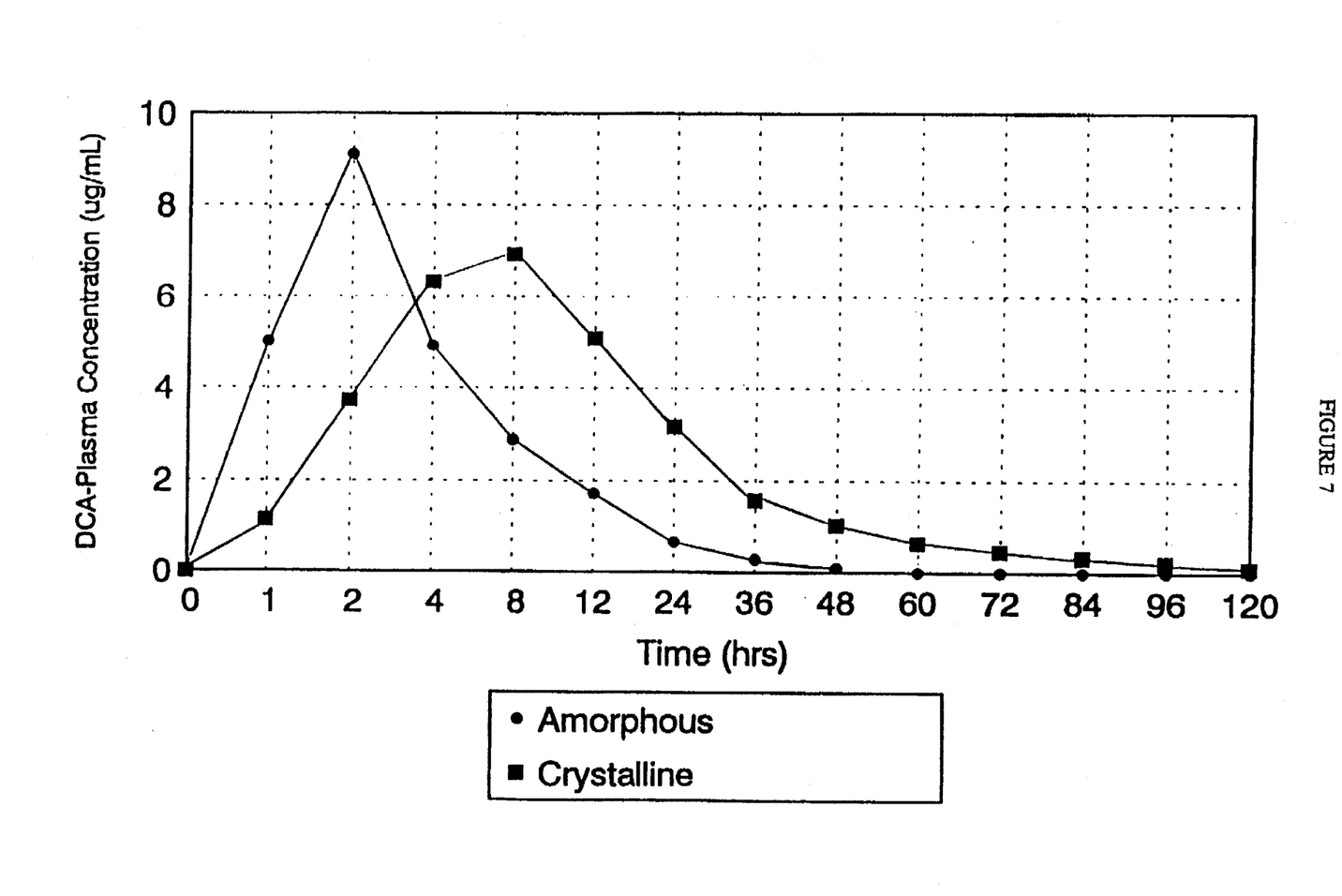

The results are shown graphically in FIG. 7 below by plotting plasma concentration of desfuroylceftiofur acetamide (DCA) versus time using average data for 6 animals/treatment. Both $t_{>0.2}$ and AUC were calculated using the predictive pharmacokinetic equation method and the direct graphical method of trapezoids (AUC) and log-linear interpolation ($t_{>0.2}$) The $t_{>0.2}$ for crystalline ceftiofur free acid was 101 hours after dosing whereas the amorphous ceftiofur free acid gave a value of 41 hours. Additionally, the AUCs comparison shows that the crystalline ceftiofur free acid has a value more than twice that of the amorphous ceftiofur free acid previously claimed (183 mcg hr/ml versus 70 mcg hr/ml). This is especially important in light of the two forms obtaining statistically equivalent peak concentrations (9.1 mcg/ml for the amorphous ceftiofur free acid versus 7.3 mcg/ml for the crystalline ceftiofur free acid). By the secondary measure of sustained release, time to peak concentration ($t_{max}$), the crystalline form shows delayed release as compared to the amorphous form of ceftiofur free acid (8 hours versus 2 hours).

EXAMPLE 9

Figure 8:
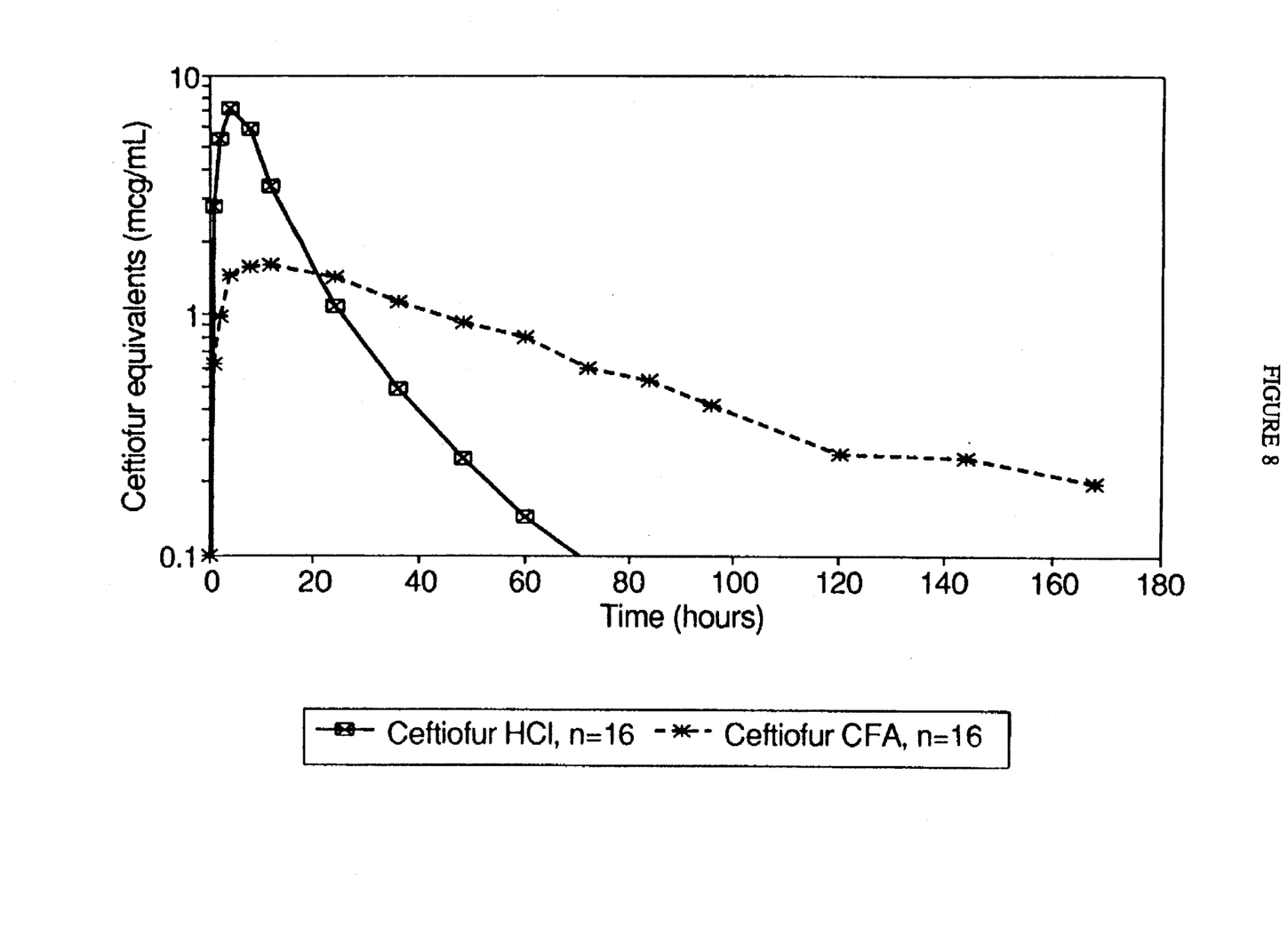

Plasma Disposition of Crystalline Ceftiofur in Oil Suspensions: Comparison of Crystalline Ceftiofur Hydrochloride and Crystalline Ceftiofur Free Acid In separate but similarly designed studies conducted in the same laboratory, crystalline ceftiofur free acid (CFA) and crystalline ceftiofur hydrochloride (HCl) suspensions were administered subcutaneously to cattle at a dose of 2.2 mg/kg body weight. In each experiment, plasma samples were obtained for up to 120 hours after drug administration for determination of ceftiofur and its metabolites. The results are shown graphically in FIG. 8 below by plotting plasma concentration (on a logarithmic scale) versus time using average data for 16 animals/treatment. The primary decision criteria (that most related to efficacy) was considered to be the time that the ceftiofur metabolite concentrations remained above 0.2 mcg/ml ($t_{>0.2}$). Less important parameters measures included "area under the concentration-time curve" (AUC) for each treatment and time to peak and peak concentrations.

The AUC values were comparable for the two crystal forms (103.3 for the crystalline hydrochloride and 121.3 for the crystalline free acid). However, the parameter, $t_{>0.2}$, used to describe sustained release effect was significantly greater for the free acid crystal form (121.6 hours versus 38.5 hours). Like the amorphous material cited in Example 8, the crystalline hydrochloride showed faster release when compared to the crystalline free acid by the criteria $t_{max}$ (2 hours for the hydrochloride versus 8 hours for the crystalline).

BRIEF DESCRIPTION OF DRAWINGS

FIG. 1

FTIR Spectrum of Amorphous Ceftiofur Free Acid

FIG. 2

FTIR Spectrum of Crystalline Ceftiofur Free Acid

FIG. 3

XRD Diffraction Pattern of Amorphous Ceftiofur Free Acid

FIG. 4

XRD Diffraction Pattern of Crystalline Ceftiofur Free Acid

FIG. 5

XRD Diffraction Pattern of Crystalline Ceftiofur Free Acid

FIG. 6

Ceftiofur Oil Suspension Dissolution Comparison

FIG. 7

Plasma Disposition Profile of Ceftiofur Free Acid: Amorphous vs. Crystalline

FIG. 8

Ceftiofur in Plasma: Ceftiofur HCl vs. Ceftiofur CFA

FIG. 9

Ceftiofur Dissolution Rate Comparison

FORMULA CHART

Formula I

Formula IA

Formula II

TABLE 1

CHARACTERISTIC XRD DIFFRACTION PEAKS OF CRYSTALLINE CEFTIOFUR FREE ACID

| Two-Theta Angle** (degree) | d-Spacing (Angstrom) | Relative Intensity#, ∞ (arbitrary) |
|---|---|---|
| 38.45* | 2.339 | 65 |
| 38.20 | 2.354 | 25 |
| 36.85 | 2.437 | 13 |
| 35.35 | 2.537 | 25 |
| 32.35 | 2.765 | 26 |
| 28.30 | 3.151 | 31 |
| 27.80 | 3.206 | 28 |
| 27.15 | 3.282 | 40 |
| 25.65 | 3.470 | 95 |
| 25.25 | 3.524 | 68 |
| 24.45 | 3.638 | 53 |
| 23.50 | 3.783 | 40 |
| 21.60 | 4.111 | 60 |
| 21.40 | 4.149 | 48 |
| 19.85 | 4.469 | 70 |
| 18.15 | 4.884 | 56 |
| 15.30 | 5.786 | 100 |
| 14.50 | 6.104 | 37 |
| 10.55 | 8.379 | 35 |
| 8.60 | 10.273 | 29 |

*: diffraction peak of the Aluminum sample tray
**: ±0.10°
: The relative intensity for each peak is determined by ratioing its intensity to that of the strongest peak at 15.3° angle as 100.
∞: The peaks that are reported in this table are those having a relative intensity greater than 10.

TABLE II

COMPARISON OF PROPERTIES OF CRYSTALLINE CEFTIOFUR FREE ACID, AMORPHOUS CEFTIOFUR FREE ACID, AND CRYSTALLINE CEFTIOFUR HYDROCHLORIDE

| Properties | Crystalline Free Acid | Amorphous Free Acid | Crystalline Hydrochloride Salt |
|---|---|---|---|
| Thermal Stability (DSC decomposition | onset = 212° C. peak = 222° C. | onset = 144° C. peak = 177° C. | onset = 187° C. peak = 192° C. |

TABLE II-continued

COMPARISON OF PROPERTIES OF CRYSTALLINE CEFTIOFUR FREE ACID, AMORPHOUS CEFTIOFUR FREE ACID, AND CRYSTALLINE CEFTIOFUR HYDROCHLORIDE

| Properties | Crystalline Free Acid | Amorphous Free Acid | Crystalline Hydrochloride Salt |
|---|---|---|---|
| temperature) | | | |
| Solubility-pH7 | ≈8 mg/mL | ≈100 mg/mL | ≈100 mg/mL |
| Dissolution Rate* | Slow | Fast | Fast |
| In Vivo Release | Prolonged | Fast | Fast |
| Purity | High | Low | High |
| Stability in Aqueous Formulations (>90% initial potency) | Stable for 6 months | Unstable in 6 weeks | Unstable in 6 weeks |
| Hygroscopity | Low | High | Moderate |
| Processing | Micronizes easier | Difficult to micronize | Micronizes easier |

Figure 9:
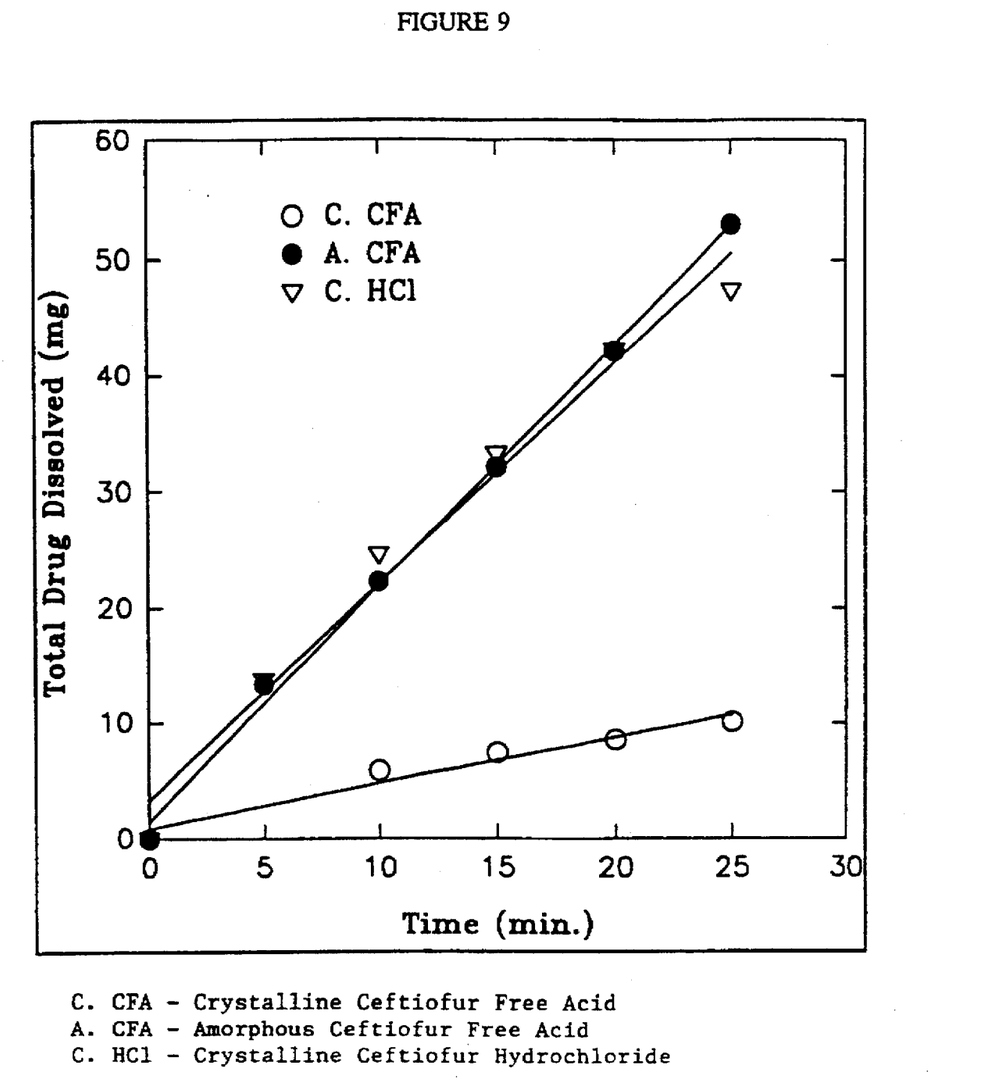

*Shown graphically in Figure 9 below.

We claim:

1. A crystalline compound of the formula I which is 7-[2-(2-amino-1,3-thiazol-4-yl)-2-methoxyimino)acetamido]-3-[(fur-2-ylcarbonyl)thiomethyl]-3-cephem-4-carboxylic acid.

2. The compound of claim 1 exhibiting essentially the following x-ray powder diffraction properties:

| Two-Theta Angle** (degree) | d-Spacing (Angstrom) | Relative Intensity#, ∞ (arbitrary) |
|---|---|---|
| 38.45* | 2.339 | 65 |
| 38.20 | 2.354 | 25 |
| 36.85 | 2.437 | 13 |
| 35.35 | 2.537 | 25 |
| 32.35 | 2.765 | 26 |
| 28.30 | 3.151 | 31 |
| 27.80 | 3.206 | 28 |
| 27.15 | 3.282 | 40 |
| 25.65 | 3.470 | 95 |
| 25.25 | 3.524 | 68 |
| 24.45 | 3.638 | 53 |
| 23.50 | 3.783 | 40 |
| 21.60 | 4.111 | 60 |
| 21.40 | 4.149 | 48 |
| 19.85 | 4.469 | 70 |
| 18.15 | 4.884 | 56 |
| 15.30 | 5.786 | 100 |
| 14.50 | 6.104 | 37 |
| 10.55 | 8.379 | 35 |
| 8.60 | 10.273 | 29 |

*: diffraction peak of the Aluminum sample tray
**: ±0.10°
: The relative intensity for each peak is determined by ratioing its intensity to that of the strongest peak at 15.3° angle as 100

| Two-Theta Angle** (degree) | d-Spacing (Angstrom) | Relative Intensity#, ∞ (arbitrary) |
|---|---|---|

∞: The peaks that are reported in this table are those having a relative intensity greater than 10.

3. In a pharmaceutical composition comprising a compound of the formula I wherein the improvement is characterized by:

at least forty percent (40%) of the compound of formula I is crystalline.

4. The composition of claim 3 which further comprises a pharmaceutically acceptable carrier or excipient.

5. The composition of claim 3 wherein the improvement is characterized by at least fifty percent (50%) of the compound of formula I is crystalline.

6. The composition of claim 5 wherein the improvement is characterized by at least seventy percent (70%) of the compound of formula I is crystalline.

7. A pharmaceutical composition which comprises a crystalline compound of the formula I 8. The composition of claim 7 which further comprises a pharmaceutically acceptable carrier or excipient.

9. The composition of claim 7 wherein the composition is sustained-release.

10. The composition of claim 7 which further comprises from about 20 to 200 mg/ml of the compound of formula I.

11. The composition of claim 7 in which the composition is administered by subcutaneous or intramuscular injection.

12. The composition of claim 7 wherein the composition is nonaqueous.

13. The composition of claim 12 wherein the nonaqueous composition is an oil.

14. The composition of claim 13 wherein the oil is selected from the group consisting of: corn oil, peanut oil, sesame oil, olive oil, palm oil, safflower oil, soybean oil, cottonseed oil, rapeseed oil, sunflower oil and mixtures thereof.

15. A process for preparing a crystalline free acid of the formula I which comprises the steps of:

a) combining a solution of the compound of formula I in a water miscible solvent with water, which is at a temperature of between 20° C. and 60° C.

16. The process of claim 15 wherein the solvent is selected from the group consisting of acetone, tetrahydrofuran (THF), and ethanol.

17. The process of claim 16 wherein the solvent is tetrahydrofuran (THF).

18. The process of claim 15 wherein the water is at a temperature of between 40° C. and 60° C.

19. The process of claim 18 wherein the water is at approximately 50° C.

20. The process of claim 17 wherein the ratio of water to THF solution of the compound of formula I is in the range of 10:1 to 2:1.

21. The process of claim 20 wherein the ratio of water to THF solution of the compound of formula I is approximately 3:1.

22. The process of claim 15 which further comprises:

b) stirring the mixture resulting from step a) for a time period of between thirty (30) minutes and twenty-four (24) hours.

23. The process of claim 22 wherein the time period is between thirty (30) minutes and four (4) hours.

24. The process of claim 23 wherein the time period is between thirty (30) minutes and one (1) hour.

* * * * *